United States Patent [19]

Ward et al.

[11] 4,164,524
[45] Aug. 14, 1979

[54] TREATMENT OF BLOOD CONTAINING VESSELS

[76] Inventors: Charles A. Ward, 25 Borden St., Toronto, Canada, M5S 2M8; Walter Zingg, 92 Highbourne Rd., Toronto, Canada, M5P 2J6

[21] Appl. No.: 814,610

[22] Filed: Jul. 11, 1977

Related U.S. Application Data

[63] Continuation of Ser. No. 581,336, May 27, 1975, abandoned.

[30] Foreign Application Priority Data

May 31, 1974 [CA] Canada ............................. 201409

[51] Int. Cl.$^2$ ............................................. B29C 25/00
[52] U.S. Cl. ........................................... 264/39; 3/1.4; 128/DIG. 22; 422/44; 264/102; 264/233; 264/340
[58] Field of Search ................ 264/102, 101, 340, 39, 264/344, 232, 233, 169; 23/258.5 R, 258.5 A; 3/1.4; 55/16; 128/DIG. 22

[56] References Cited

U.S. PATENT DOCUMENTS

| 3,274,750 | 9/1966 | Robb | 55/16 |
| 3,450,502 | 6/1969 | Hymes | 23/258.5 A |
| 3,577,291 | 5/1971 | Uchida | 264/98 |
| 3,585,647 | 6/1971 | Gajewski et al. | 3/1.4 |
| 3,614,856 | 10/1971 | Sanz et al. | 55/16 |
| 3,651,616 | 3/1972 | Blanchard | 23/258.5 A |
| 3,833,013 | 9/1974 | Leonard | 23/258.5 A |

Primary Examiner—Jeffery R. Thurlow

[57] ABSTRACT

Method and apparatus are provided for treating one surface of a wall of articles to be used in contact with blood. A solution which is compatible with blood is brought into contact with the surface and a partial vacuum is applied to the wall for a predetermined time period. This partial vacuum causes gas nuclei trapped in irregularities in the surface to permeate through the wall. Consequently when blood displaces the solution there is less likelihood of blood platelets being trapped on the surface with eventual blood clotting.

5 Claims, 3 Drawing Figures

TREATMENT OF BLOOD CONTAINING VESSELS

This is a continuation of application Ser. No. 581,336 filed May 27, 1975, now abandoned.

This invention relates to a method and apparatus for use in reducing the adhesion of blood platelets to the surface of synthetic gas permeable materials used to fabricate containers for blood.

When the surface of a gas permeable synthetic material such as a vessel or tube is exposed to blood the adhesion of blood platelets to the surface of the material is one of the initiating steps leading to the formation of blood clots. Investigation of the problem indicates that blood platelet adhesion is related to the presence of microscopic gas nuclei present in minute imperfections in the surface of the material exposed to the blood.

It will be appreciated that blood clotting is a relatively serious problem not only when using medical equipment such as a heart-lung machine, but also in the storage of blood for later use in treating patients. In many cases the blood must be treated with an anticoagulant chemical such as heparin to prevent coagulation.

In the past gas nuclei were removed from the surface of vessels or tubes used to contain blood by thoroughly washing the insides of the vessels or tubes with a solution such as distilled water or other blood compatible solution prior to introducing blood into the container. While this process was capable of removing some of the surface trapped gas nuclei it was unsuccessful in removing a sufficient number of gas nuclei to satisfactorily eliminate the problem of platelet adhesion to the container surface. This often resulted in excessive blood clotting.

Accordingly it is an object of the present invention to provide an improved method for treating the surface of synthetic gas permeable materials to remove gas nuclei trapped in surface irregularities. It is also an object of the present invention to provide a process which is relatively simple, which is economical to expedite, and which is applicable to a wide variety of container shapes. It is a further object of the present invention to provide an apparatus to perform the process of treating the surface of synthetic gas permeable materials to remove gas nuclei trapped in surface irregularities.

According to one aspect of the present invention a method is provided for treating one surface of a wall of articles to be used in contact with blood. A solution which is compatible with blood is brought into contact with the surface and a partial vacuum is applied to the wall for a predetermined time period. This partial vacuum causes gas nuclei trapped in irregularities in the surface to permeate through the wall. Consequently when blood displaces the solution there is less likelihood of blood platelets being trapped on the surface with eventual blood clotting.

The method and apparatus used to perform the method will be better understood with reference to the drawings in which.

Figure 1:
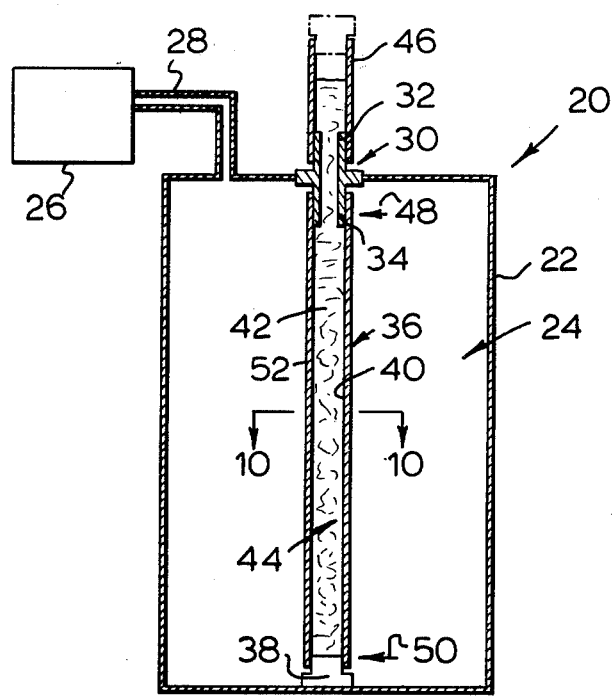
FIG. 1 is a diagrammatic front sectional view of preferred embodiment of an apparatus according to the present invention for use in treating the internal surface of a tube made from a synthetic gas permeable material.
Figure 2:
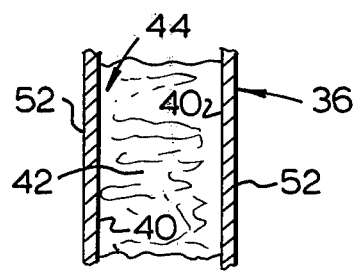
FIG. 2 is an enlarged view of a portion of FIG. 1 in the region of lines 10—10 of FIG. 1.

Reference is first made to FIGS. 1 and 2 with particular reference initially to FIG. 1. Apparatus 20 according to the invention includes a rigid receptacle 22 defining an enclosed space 24 within which a vacuum is generated by a vacuum pump 26. The vacuum pump is connected to the receptacle 22 by means of a pipe 28 and an inlet port 30 is provided through one side of receptacle 22. The inlet port includes a conventional vacuum seal and defines respective internal and external connector portions 32 and 34.

A continuous length of tubing 36 which is to be treated in the apparatus 20 is placed within the enclosed space 24 such that one end of the tubing 36 is fitted to the connector portion 34 and the other end of the tubing is sealed by a closure 38. The closure 38 may be fixed to a bottom wall of receptacle 22 or it may be separate from the receptacle.

The entire interior surface 40 (FIG. 2) of the tubing 36 is exposed to a solution 42 which may be a phosphate buffer solution or some other solution which is compatible with blood. The solution 42 is introduced into the interior space 44 within the tubing 36 via inlet port 30 and a tube 46 which is filled to external connector portion 32. All of the space 44 between arrows 48 and 50 in FIG. 1 must be filled with the solution 42. After filling the interior space 44 as described above, the end of tube 46 remote from connector portion 32 may be left open to the atmosphere or preferably sealed (as shown in ghost outline).

Vacuum pump 26 is used to remove air from the enclosed space 24 thereby exposing the exterior surface 52 of tubing 36 to a partial vacuum. The vacuum pump 26 must be capable of generating a predetermined minimum vacuum level in the enclosed space 24. Once the required vacuum level has been created in space 24 this vacuum level must be maintained for a predetermined period of time.

Due to the presence of the vacuum in space 24 the gas nuclei trapped in surface irregularities of the interior surface 40 of tubing 36 diffuse through the gas permeable walls of the tubing into enclosed space 24 where they are removed by vacuum pump 26. The solution 42 introduced into interior space 44 may be degassed before use in any of a variety of ways familiar to those skilled in the art. However, it is not necessary to perform this degassing operation because dissolved gas in the solution can be removed during the treatment of tubing 36 in the same manner as air trapped in the irregularities of the surface 40 of tube 36. However the use of a degassed solution will tend to reduce the time needed to treat the tubing.

The presence of a vacuum in enclosed space 24 provides a pressure gradient which forces trapped air nuclei to diffuse through the walls of tubing 36 into space 24. The space previously occupied by the gas nuclei is filled by the solution 42. In this manner the majority of gas nuclei trapped in surface irregularities of the interior surface 40 of tubing 36 are replaced by solution 42.

After tubing 36 has been treated as described above it may be used to contain blood. The blood is introduced into the interior space 44 of the tubing 36 in such a way as to displace the solution 42 without introducing air.

In the preferred embodiment of the present invention tubing 36 is made from silicone rubber sold under a variety of names including SILICHEM (trade mark) or SILASTIC (trade mark). Tubing 36 has a wall thickness of approximately 0.051 inches to 0.063 inches. For this particular wall thickness and a vacuum level of 1 mm of mercury absolute in space 24 approximately 20 hours is required to ensure adequate removal of gas nuclei from the interior surface 40 of tubing 36. It will be appreciated that an interrelationship exists between the vacuum level required in space 24, the time period during which the vacuum must be maintained and the wall thickness of tubing 36. The greater the wall thickness the longer the period of time the vacuum must be held for a given vacuum level, and for a given wall thickness the length of the time period during which the vacuum must be maintained may be reduced if the vacuum level is increased. For most common wall thickness the tubing 36 will require a minimum vacuum level for removal of gas nuclei on interior surface 40. Below this level no noticeable removal of gas nuclei trapped on interior surface 40 will occur.

Figure 3:
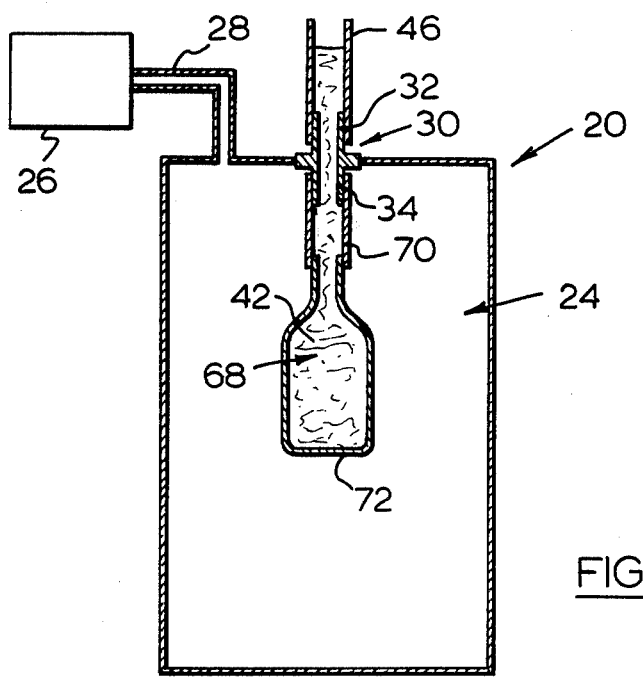
FIG. 3 shows the apparatus of FIG. 1 used to treat a vessel made from a synthetic gas permeable material.

Reference is next made to FIG. 3 which shows the apparatus 20 used to treat a vessel 72. The reference numerals employed in FIG. 3 are the same as those used in FIG. 1 for similar elements. The following description of the treatment of vessel 72 will be abbreviated due to the similarity of the treatment of the tubing 36 described above in connection with FIG. 1.

Vessel 72 is shown as a convention bottle-shaped structure. However, the vessel may take any form including that of a flexible pouch. The neck of the vessel 72 may be coupled to the connector portion 34 by a short length of tubing 70. The method of coupling the vessel to connector portion 34 is not critical and any other suitable method may be used. The solution 42 is introduced into the interior 68 of the vessel 72 via tubing 46, port 30 and a tubing 70. As in the case of the tubing 36 (see FIG. 1) the vessel 72 must be completely filled with the solution 42 so that all of the interior surface of the vessel is exposed to solution 42.

The exterior surface of vessel 72 is exposed to a vacuum generated by the vacuum pump 26. If the vessel 72 has a wall thickness equal to that of tubing 36 the same vacuum levels described above with reference to FIG. 1 may be used. As in the case of tubing 36 the minimum vacuum level necessary must be maintained for a period of time which is dependent on the wall thickness of the vessel 72.

After the vessel 72 has been treated it may be disconnected from tubing 70 and a closure such as a plastic stopper (not shown) inserted into the neck of the vessel 72. The solution 42 must remain in the vessel 72 until the vessel is used to hold blood. The blood is introduced into the interior 68 of the vessel via the neck in a manner adapted to displace the solution 42 without allowing air to enter the vessel.

Ideally when a vessel is treated by the method of the present invention the entire interior surface of the vessel which will come into contact with blood should be treated. In the case of the tubing 36 shown in FIG. 1 the end portions fitted to connector portion 34 and to closure 38 are left untreated since the interior surface of these portions of the tube are not in contact with the solution 42. In practice this is not a problem because the tube will ordinarily be fitted to other connectors (not shown) when used to carry blood. However, the untreated end portions of tube 36 may be cut away prior to use if the entire length of tubing must be treated. In the case of vessel 72 this is less of a problem because the untreated neck portion of the vessel will ordinarily not be exposed to blood when the blood is introduced into the vessel. The blood may be introduced into vessel 72 by a suitably treated tube having an end which is placed inside the vessel and which extends into the vessel adjacent to the bottom portion of the vessel (not shown). When the vessel is filled a closure is fitted into the neck so that the blood never contacts the untreated portion of the neck.

It will be appreciated that the present invention can also be used to treat the exterior surface of an article such as a vessel or a tube. In this case the interior surface of the article is exposed to a partial vacuum as indicated in ghost outline in FIG. 3. The exterior surface of the article is exposed to solution 42. Provision must be made to prevent the article from collapsing due to the internal vacuum.

What we claim is:

1. A method of treating at least a portion of a first surface of a gas permeable wall of the type used in gas permeable medical tubing, vessels and the like, the surface having small irregularities containing gas nuclei and the method comprising the steps:

bringing a solution which is compatible with blood into contact with said first surface at least to the extent that the solution is in contact with all of said portion of the first surface; and applying a partial vacuum to a second side of the wall to thereby create a pressure gradient from said first side to said second side of the wall for a predetermined time period to enhance permeation of the gas nuclei trapped in said irregularities so that these gas nuclei pass through the wall and so that priming solution is drawn at least partly into said irregularities whereby a new first surface is created consisting partly of said portion of said first surface and partly of solution trapped in said irregularities, the new first surface being substantially free of gas nuclei so that when the main body of priming solution is displaced by blood the number of blood to gas nuclei interfaces is limited to thereby significantly diminish the possibility of platelet adhesion.

2. The method as claimed in claim 1 in which said first surface is the inner surface of a wall of an article such as a length of tubing, a vessel and the like.

3. The method as claimed in claim 1 in which said first surface is the outer surface of the wall of an article adapted to be immersed in blood in use such that the blood will be in contact with said outer surface.

4. The method as claimed in claim 1 and further comprising the step of degassing the solution prior to filling the article with the solution.

5. The method as claimed in claim 3 and further comprising the step of degassing the solution prior to filling the article with the solution.

* * * * *